(12) United States Patent
Dorbon et al.

(10) Patent No.: US 6,242,662 B1
(45) Date of Patent: Jun. 5, 2001

(54) PROCESS FOR OBTAINING BUTENE-1

(75) Inventors: Michel Dorbon, Paris; François Hugues, Vernaison; Jean-Charles Viltard, Vienne; Blaise Didillon, Rueil Malmaison; Alain Forestiere, Vernaison, all of (FR)

(73) Assignee: Institut Francais du Petrole, Rueil-Malmaison (FR)

( * ) Notice: Subject to any disclaimer, the term of this patent is extended or adjusted under 35 U.S.C. 154(b) by 0 days.

(21) Appl. No.: 09/229,958

(22) Filed: Jan. 14, 1999

(30) Foreign Application Priority Data

Jan. 14, 1998 (FR) .................................................. 98 00397

(51) Int. Cl.$^7$ ........................................................ C07C 5/25
(52) U.S. Cl. ............................................ 585/670; 585/664
(58) Field of Search ...................................... 585/670, 664

(56) References Cited

U.S. PATENT DOCUMENTS 5,087,780 * 2/1992 Arganbright ........................... 585/259

FOREIGN PATENT DOCUMENTS

| 0 129 900 | 1/1985 | (EP) . |
|---|---|---|
| 2 528 033 | 9/1983 | (FR) . |
| 57-131729 | * 8/1982 | (JP) . |
| 1595829 | * 9/1990 | (SU) . |

* cited by examiner

Primary Examiner—Jerry D. Johnson
Assistant Examiner—Thuan D. Dang
(74) Attorney, Agent, or Firm—Millen White Zelano & Branigan

(57) ABSTRACT

For obtaining butene-1 from butene-2, a charge containing at least one of the isomers of butene-2 is introduced into a distillation zone linked to a hydro-isomerization zone. Part of the effluent from the bottom of the distillation column is removed from the distillation zone, heated in a heat exchanger and passed into an external hydro-isomerization zone. The hydro-isomerization effluent is removed from the hydro-isomerization zone, cooled in a heat exchanger, and then reintroduced into the distillation zone. Effluent containing butene-1 is withdrawn from the top of the column of the distillation zone.

22 Claims, 2 Drawing Sheets

PROCESS FOR OBTAINING BUTENE-1

FIELD OF THE INVENTION

The present invention relates to the field of the production of but-1-ene. But-1-ene is an important compound for the synthesis of copolymers, for example, with ethylene for linear low density polyethylenes, or for the synthesis of butene oxide.

BACKGROUND OF THE INVENTION

A study of the prior art has revealed two documents which describe processes wherein at least one of the products isolated is but-1-ene, these being patents FR-B-2 527 201 and EP-B-0 129 900. The patent FR-B-2 527 201 describes a process in several steps starting with a charge of hydrocarbons having 4 carbon atoms. After undergoing several treatments including an etherification reaction with an aliphatic alcohol, then several treatments for the separation of the various constituents of the mixture, but-1-ene is recovered in a top fraction of a distillation column, the bottom fraction being composed of the other compounds and of non recovered but-1-ene. Said bottom fraction is then passed to an isomerization zone where it is partly converted to isobutene. The patent EP-B-0 12 900 describes a process for producing but-1-ene by isomerization starting with a mixture of hydrocarbons containing but-2-enes. This document raises an important problem which is the service life of the isomerization catalyst and hence of the regeneration of said catalyst. The type of catalyst used is an acid catalyst and the operating conditions of the reaction require a reaction temperature of the order of 250° C. to 400° C. Moreover, this process generates isobutene which is difficult to separate from but-1-ene, even if this compound is present only in traces.

SUMMARY OF THE INVENTION

The present invention relates to a process in several steps for obtaining but-1-ene from a charge comprising hydrocarbons having 4 carbon atoms per molecule including at least one of the isomers of but-2-ene (but-2-ene occurs in the cis and trans forms), said process comprising at least one distillation step and at least one hydro-isomerization step, these steps possibly also being merged.

The advantages of the present invention include the possibility of obtaining but-1-ene with yields greater than 100% by mass with respect to the but-1-ene present in the charge. In comparison with the isomerization processes, it will be noted that the use of a hydro-isomerization catalyst makes it possible to operate at significantly lower temperatures. This lower hydro-isomerization temperature means that the cracking rate is not detectable. The formation of coke, which is the main factor responsible for deactivation of the catalyst, is also very low.

The catalyst used is highly selective of the isomerization reaction with respect to the hydrogenation reactions. Moreover, the amount of hydrogen required for the hydro-isomerization reaction is very small. The losses due to the hydrogenation of butenes are therefore very small and it is not vital to add a means of separating hydrogen from the effluent leaving the hydro-isomerization reactor. However, embodiments in which a means of isolating hydrogen if the effluent leaving the hydro-isomerization reactor contains hydrogen are not excluded from the scope of the present invention.

The invention relates to a process for obtaining but-1-ene wherein a charge containing at least one of the isomers of but-2-ene is passed to a distillation zone linked with a hydro-isomerization zone.

The invention also relates to a device for implementing the process according to the invention.

The charge treated by the process according to the invention may be a cut containing hydrocarbons having 4 carbon atoms, including at least one of the isomers of but-2-ene. It may originate, for example, from steam cracking, fluid catalytic cracking (FCC) or skeletal isomerization.

The charge generally contains butadiene, butanes (n-butane and isobutane), butenes (isobutene, but-1-ene and but-2-enes, cis and trans forms). This charge may be introduced into the distillation zone of the process according to the invention without a prior treatment. However, certain uses require high-purity but-1-ene. For these, it is necessary, therefore, to separate but-1-ene from the products whose boiling point is close to or lower than the boiling point of but-1-ene. Said products are generally butadiene, isobutane and isobutene.

In order to remove butadiene from the mixture, it generally undergoes selective hydrogenation in which case the effluent leaving the selective hydrogenation reactor contains only butanes (n-butane and isobutane), butenes (isobutene, but-1-ene and but-2-ene, cis and trans forms), and traces of butadiene.

Isobutene is usually removed by extraction or by using it as a reagent of a reaction. Isobutene may, for example, be oligomerized, for example, according to a process known as "Polynaphta" developed by the Applicant. It may also react with certain alcohols according to etherification reactions in order to give, for example, methyl tert.butylether (MTBE) or ethyl tert.-butylether (ETBE). Isobutane is generally removed by distillation.

The treatments for removing butadiene and isobutene may be carried out on a charge before its introduction into the distillation zone of the process according to the invention, or on the effluent from the top of the column of the process according to the invention. In preference, they will be carried out before the charge is introduced into the distillation zone. Isobutane is generally removed in the top effluent of the process according to the invention.

DETAILED DESCRIPTION OF THE INVENTION

Figure 1:
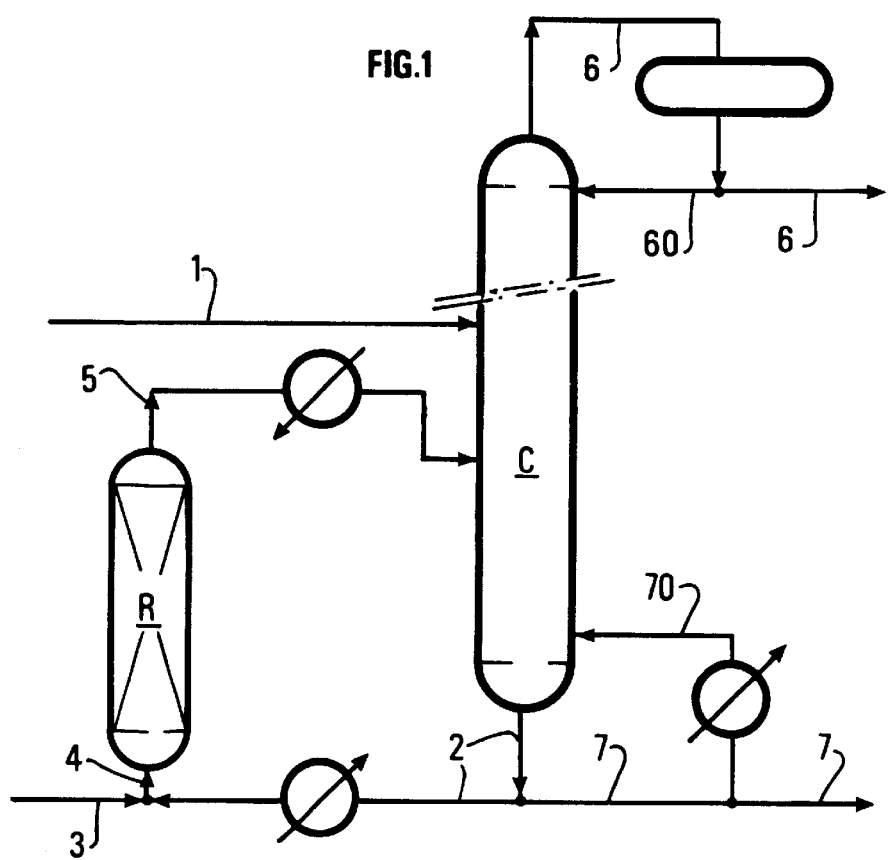
FIG. 1 represents a simple embodiment of the process according to the invention.

The invention relates to a process for obtaining but-1-ene wherein a charge containing at least one of the isomers of but-2-ene is passed to a distillation zone linked with a hydro-isomerization zone. The charge of the distillation zone is introduced at at least one level of the distillation column, the charge of the hydro-isomerization zone is withdrawn at the height of at least one level of the distillation zone and it represents at least a part of the liquid flowing in the distillation zone. This level of the distillation zone may also be the bottom of the distillation column. The effluent of the hydro-isomerization zone is at least partly reintroduced into the distillation zone at at least one level of reintroduction. According to the process of the invention, the top fraction of the effluent of the distillation zone contains at least but-1-ene.

The distillation zone generally comprises at least one column fitted with at least one distillation interior chosen from the group consisting of simple plates, multi-weir plates, random packings and ordered packings, of the kind known to the man skilled in the art, for example of such kind that the total overall efficiency is at least equal to five theoretical stages. In the cases known to the man skilled in the art where the use of a single column poses problems, it is generally preferable to divide the said zone so as finally to use at least two columns which, placed end to end, form said zone, that is, the rectification zone, the optional reaction zone and the stripping zone are distributed over the columns.

The distillation zone is linked with a hydro-isomerization zone in which at least part of the but-2-enes present in the charge are converted to but-1-ene. Said hydro-isomerization zone may be outside the distillation zone or incorporated in the distillation zone; it may also be partly outside the distillation zone and partly incorporated in the distillation zone.

The hydro-isomerization zone of the process according to the invention may be defined as a zone where a reaction is carried out in the presence of a hydro-isomerization catalyst and a gas flow containing hydrogen.

The hydro-isomerization zone generally comprises at least one catalytic hydro-isomerization bed containing a hydro-isomerization catalyst. Preferably, the reaction zone comprises 1 to 6 catalytic beds. The hydro-isomerization zone brings about at least partially the hydro-isomerization of but-2-enes to but-1-ene.

The hydro-isomerization reaction zone may be at least partly outside the distillation zone. In this case it comprises at least one reactor, preferably a single reactor. According to this embodiment, the process according to the invention makes it possible to isomerize but-2-enes to but-1-ene outside the distillation zone, optionally under pressure and/or temperature conditions which are different to those used in the column.

The charge of the distillation zone may be introduced at any level of the distillation column, for example, at several levels of introduction, but preferably at a single level of the distillation column. It would not be beyond the scope of the present invention to introduce into the distillation zone several charges of different compositions at several levels of introduction.

Starting from a charge comprising hydrocarbons having 4 carbon atoms, including butadiene, butanes (n-butane and isobutane), butenes (isobutene, but-1-ene and but-2-enes in the cis and trans forms), the products recovered from the top of the distillation column are mainly butadiene, isobutane, isobutene and but-1-ene, and the bottom products recovered are mainly n-butane and but-2-enes.

Each stage of the column may be defined by a pressure-temperature combination, and to each stage there corresponds a composition of the mixture of the various constituents. Thus, the mixtures rich in but-1-ene are situated in the upper stages of the column (top of the column), and the mixtures rich in but-2-enes are found in the lower stages of the column (bottom of the column).

The charge of the hydro-isomerization zone is withdrawn at at least one withdrawal level of the distillation zone, preferably at a single level thereof. The withdrawal from the distillation column is generally carried out at a level where the value of the ratio of the quantity of but-2-enes to the quantity of but-1-ene is greater than its value at the thermodynamic equilibrium at the entrance to the reaction zone. The withdrawal from the distillation column is generally carried out at a level situated below the level of introduction of the charge into said distillation column, more particularly, the withdrawal may be carried out at the bottom of the distillation column.

The withdrawal from the distillation column carried out at the bottom of the distillation column may be only partly introduced into the hydro-isomerization zone. Usually, provision is also made for the removal of another part of this fraction. Moreover, if the hydro-isomerization zone is completely outside the distillation zone, the withdrawal from the distillation zone may undergo a treatment before being introduced into the hydro-isomerization zone. This treatment may be, for example, a separation of the various constituents of the mixture, purification of the effluent, a reaction other than hydro-isomerization.

The hydro-isomerization reaction is as follows:
[but-1-ene→but-2-enes (cis and trans)] but-2-enes (cis and trans)→but-1-ene Apart from the hydro-isomerization reaction noted above, secondary hydrogenation reactions which produce essentially butanes in small quantities take place, these reactions contributing to reducing the but-1-ene yield. However, as the amount of hydrogen required for hydro-isomerization is very small, it is important not to introduce too great an excess of hydrogen; moreover, a catalyst which is highly selective in favour of isomerization will be chosen.

The hydro-isomerization reaction is carried out in the presence of hydrogen with a supported catalyst comprising generally at least one metal chosen from the group consisting of nickel and the noble metals of group VIII such as ruthenium, rhodium, palladium, osmium, iridium and platinum. This catalyst may be used as it is or preferably deposited on a support.

A supported catalyst comprising palladium is used most often. The noble metal content of the catalyst is usually about 0.01 to 2% by mass.

Said catalyst is usually treated with a compound containing sulfur, then with hydrogen before being used in the hydro-isomerization zone. The metal is advantageously in the reduced form, at least for 50% of its total mass.

If nickel is used, the proportion of nickel with respect to the total mass of the catalyst is about 5 to 70%, and preferably about 10 to 70%. Moreover, the catalyst used is generally such that the average size of the nickel crystallites is less than 10 nm, preferably less than 8 nm and even more preferably less than 6 nm. However, any other hydro-isomerization catalyst known to the man skilled in the art may also be chosen. The catalyst is generally sulfurized in situ or ex situ in such a way that the sulfur is chemisorbed on at least part of the metal.

The support is generally chosen from the group consisting of alumina, alumino-silicates, silica, zeolites, activated carbon, clays, high-alumina cements, oxides of rare earths and alkaline-earth oxides, on their own or in mixtures. It is preferable to use a support based on alumina or silica, with a specific surface of about 1 to 300 $m^2/g$, preferably about 5 to 100 $m^2/g$.

Non-limiting examples of catalysts which may be used within the scope of the present invention include commercial catalysts such as that sold by Catalysts and Chemicals under the reference C-31, that sold by Girdler Corporation under the reference G-55 or, preferably, those sold by Procatalyse under the references LD-265, LD-265S, LD-267 and LD-267R.

The hydro-isomerization reaction is carried out in the presence of hydrogen, which hydrogen may originate from any sources producing hydrogen in a purity of at least 50% by volume, preferably in a purity of at least 80% by volume and even more preferably in a purity of at least 90% by volume.

If the hydro-isomerization zone is incorporated at least partly in the distillation zone, the operating conditions of the said incorporated part are associated with the operating conditions of the distillation. In that case it is carried out under an absolute pressure of about 1 to 50 bar, preferably about 2 to 30 bar and even more preferably about 4 to 15 bar (1 bar=$10^5$ Pa), with a reflux ratio of about 1 to 70 and preferably about 5 to 40. The temperature at the top of the distillation zone is about 0 to 200° C. and the temperature at the bottom of the distillation zone is generally about 5 to 250° C. The hydro-isomerization reaction is carried out under conditions which are most generally between those established at the top and at the bottom of the distillation zone, at a temperature of about 0 to 250° C., and preferably about 50 to 200° C. The liquid undergoing hydro-isomerization is fed by a gas flow comprising, preferably for the most part, hydrogen.

In the external part of the hydro-isomerization zone, the catalyst is arranged in any catalytic bed according to any technology known to the man skilled in the art under operating conditions (temperature, pressure etc.) which are either independent or not independent, preferably independent, of the operating conditions of the distillation zone.

In the part of the hydro-isomerization zone outside the distillation zone, the operating conditions are generally as follows. The absolute pressure required for this hydro-isomerization step is generally about 1 to 70 bar, preferably about 2 to 30 bar. The operating temperature of the hydro-isomerization zone is generally about 0 to 250° C., preferably about 50 to 200° C. The space velocity (defined as the volume of charge per volume of catalyst and per hour and termed VVH) within said hydro-isomerization zone, calculated with respect to the catalyst, is generally about 0.1 to 150 $h^{-1}$ and more particularly about 4 to 50 $h^{-1}$ and even more preferably about 10 to 30 $h^{-1}$. The corresponding hydrogen flow rate is such that the molar ratio $H_2$/hydrocarbons entering the hydro-isomerization zone is preferably at least equal to $10^{-5}$. This ratio is most often about $10^{-5}$ to about 3 and very frequently about $10^{-4}$ to about 1.

In the descriptions that follow, no mention is made of the detail of the apparatus well known to the man skilled in the art, such as, for example, the reboilers and reflux drums of the distillation columns. In the figures below, the lines corresponding to the admission of the reflux fractions into the column are marked 60 and the lines corresponding to the admission of the reboiled fractions into the column are marked 70.

According to FIG. 1, the charge to be treated is introduced via line 1 into a distillation zone C. The effluent from the bottom of the column is removed from the distillation zone via line 2. A part of the flow circulating in line 2 is removed from the device via line 7. The other part of the flow circulating in line 2 is reheated by means of a heat exchanger before feeding line 4 which conveys the charge to the hydro-isomerization zone R. Line 4 is also fed via line 3 with a flow containing at least hydrogen. The hydro-isomerization effluent is removed from the hydro-isomerization zone R via line 5, it is cooled by a heat exchanger, then introduced once again into the distillation zone C. The effluent from the top of the column of the distillation zone is removed via line 6.

Figure 2:
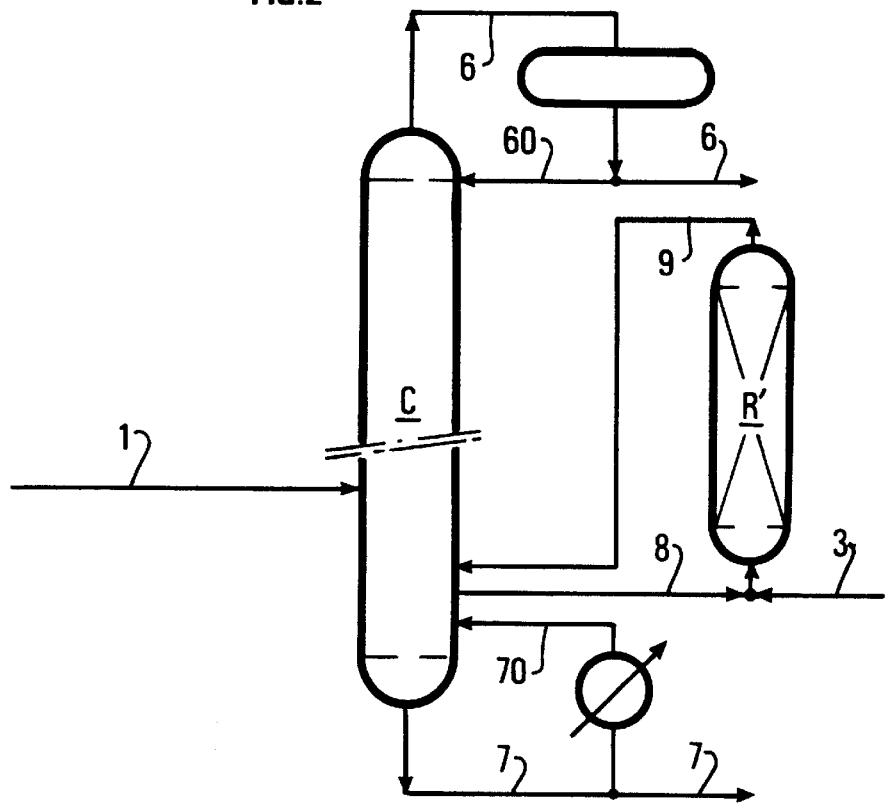
FIG. 2 represents another simple embodiment of the process according to the invention.

According to FIG. 2, the charge to be treated is introduced via line 1 into a distillation zone C. Via line 8, a withdrawal is carried out at an intermediate level of the distillation column C. Line 8 feeds the hydro-isomerization zone R', said hydro-isomerization zone R' also being fed by a flow containing hydrogen via line 3. The hydro-isomerization effluent is removed from the hydro-isomerization zone R' and reintroduced into the distillation zone C via line 9. The effluent from the bottom of the column is removed from the distillation zone C via line 7. The effluent from the top of the column of the distillation zone C is removed from the device via line 6.

Figure 3:
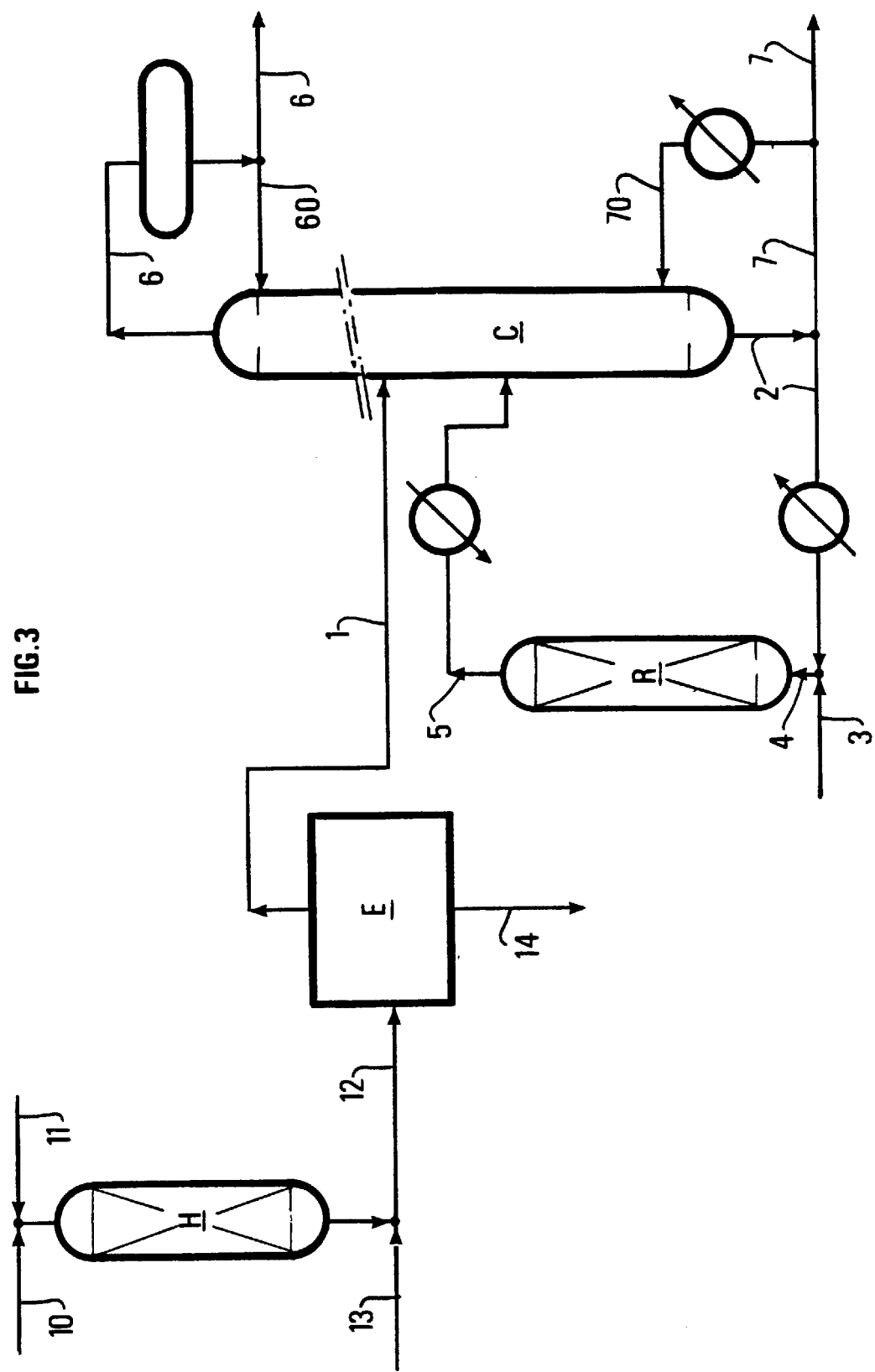
FIG. 3 represents an embodiment wherein the charge of the distillation zone undergoes several reactions beforehand.

According to FIG. 3, the charge to be treated is introduced via line 10 into a selective hydrogenation zone H, said selective hydrogenation zone H being fed with hydrogen via line 11. The effluent of zone H is removed via line 12, line 13 feeds line with a charge containing an alcohol. The charge is passed to the etherification zone linked with a separation zone E via line 12. The product of the etherification reaction E is removed via line 14 and the compounds which have not reacted are passed via line 1 to distillation zone C. The effluent from the bottom of the column is removed from the distillation zone via line 2. A part of the flow circulating in line 2 is removed from the device via line 7. The other part of the flow circulating in line 2 is reheated by means of a heat exchanger before feeding line 4 which conveys the charge to the hydro-isomerization zone R. Line 4 is also fed via line 3 with a flow containing at least hydrogen. The hydro-isomerization effluent is removed from the hydro-isomerization zone R via line 5, it is cooled by a heat exchanger then it is introduced once again into the distillation zone C. The effluent from the top of the column of the distillation zone is removed via line 6.

The entire disclosure of all applications, patents and publications, cited above and below, and of corresponding French application 98/00397, filed Jan. 14, 1998, are hereby incorporated by reference.

The examples below illustrate the invention without limiting its scope.

EXAMPLES

Within the scope of the patent application PCT WO 96/02 086, tests were carried out to describe the kinetics of the conversion of but-1-ene to but-2-enes in the case when the ratio of the quantity of but-1-ene to the quantity of but-2-enes is greater than the value it takes under conditions of thermodynamic equilibrium. The catalyst used to carry out this kinetic test is the hydro-isomerization catalyst LD-267R sold by Procatalyse.

The results of these kinetic tests were used for the conversion reaction of but-2-enes to but-1-ene in the case when the ratio of the quantity of but-2-enes to the quantity of but-1-ene is greater than the value it takes under conditions of thermodynamic equilibrium. These results made it possible to simulate the process according to the invention by means of suitable software. The software used for this simulation is sold under the name of Pro II® by SIMCI. The model chosen to simulate the examples below corresponds to an embodiment according to FIG. 1 of the present description.

In the examples below, the following abbreviations are used: <$C_4$ for hydrocarbons containing strictly fewer than 4 carbon atoms; $iC_4$ for isobutane, $iC_4^=$ for isobutene, $C_4^=1$ for but-1-ene, n $C_4$ for n-butane, $C_4^=2$ trans for trans but-2-ene, and $C_4^=2$ cis for cis but-2-ene.

Example 1

The plant comprises a distillation zone and a hydro-isomerization zone. The hydro-isomerization zone is outside the distillation column, the distillation column comprises 130 theoretical plates numbered from top to bottom. The feed is carried out at the level of plate no. 80, the hydro-isomerization reactor is fed by a draw-off situated at the level of plate no. 130 of the distillation column and the hydro-isomerization effluent is reinjected at the level of plate no. 100. The reactor contains 7 tonnes of catalyst.

The operating conditions are as follows: a reflux ratio of the column (reflux/distillate) of 17, an absolute pressure at the top of the column of 6.2 bar, an absolute pressure at the bottom of the column of 7 bar, a temperature of the feed of the column: 61.6° C., a temperature at the top of the column of 51.7° C., a temperature at the bottom of the column of 64.6° C., a reactor temperature of 75° C., an absolute pressure of the reactor of 7 bar, a total flow rate (comprising the flow rate of the charge and the flow rate of hydrogen) in the hydro-isomerization reactor of 250 kmole/h.

With this configuration and under these operating conditions, the simulation led to the results shown in the table below.

| Constituents | Column feed (kmole/h) | Top of column (kmole/h) | Bottom of column (kmole/h) |
|---|---|---|---|
| <$C_4$ | 0.8 | 0.8 | 0 |
| $iC_4$ | 12.3 | 12.4 | 0 |
| $iC_4=$ | 2.3 | 2.2 | 0 |
| $C_4=$ 1 | 80.2 | 84.3 | 1.2 |
| $nC_4$ | 109.9 | 27.0 | 83.2 |
| $C_4=2$ trans | 100.2 | 6.0 | 88.6 |
| $C_4=2$ cis | 54.7 | 0 | 54.7 |
| $H_2$ | 0.4 | 0 | 0 |
| Total | 360.8 | 132.7 | 227.7 |

This table makes it possible to calculate the but-1-ene yield at the top of the column: 105.1% by mass, and the hydrogenation yield, that is, the ratio of butanes in the effluents (top and bottom of the column)/butanes in the feed, which is 100.32% by mass. It should also be noted that the amount of hydrogen in the effluents of the top and bottom of the column is nil.

Example 2

The plant comprises a distillation zone and a hydro-isomerization zone. The hydro-isomerization zone is outside the distillation column, the distillation column comprises 130 theoretical plates, numbered from top to bottom. The feed is carried out at the level of plate no. 80, the hydro-isomerization reactor is fed by a draw-off situated at the level of plate no. 130 of the distillation column and the hydro-isomerization effluent is reinjected at the level of plate no. 100. The reactor contains 7 tonnes of catalyst.

The operating conditions are as follows: a reflux ratio of the column (reflux/distillate) of 30, an absolute pressure at the top of the column of 6.2 bar, an absolute pressure at the bottom of the column of 7 bar, a temperature of the feed of the column: 62.5° C., a temperature at the top of the column of 53.4° C., a temperature at the bottom of the column of 65.8° C., a temperature of the hydro-isomerization reactor of 75° C., an absolute pressure of the reactor of 10 bar, a flow rate in the reactor (comprising the flow rate of the charge and the flow rate of hydrogen) of 2000 kmole/h.

With this configuration and under these operating conditions, the simulation led to the results shown in the table below.

| Constituents | Column feed (kmole/h) | Top of column (kmole/h) | Bottom of column (kmole/h) |
|---|---|---|---|
| <$C_4$ | 0.8 | 0.8 | 0 |
| $iC_4$ | 12.3 | 12.4 | 0 |
| $iC_4=$ | 2.3 | 2.2 | 0 |
| $C_4=$ 1 | 80.2 | 134.9 | 0.5 |
| $nC_4$ | 109.9 | 88.8 | 21.9 |
| $C_4=2$ trans | 100.2 | 23.6 | 21.4 |
| $C_4=2$ cis | 54.7 | 0.1 | 53.8 |
| $H_2$ | 0.9 | 0 | 0 |
| Total | 360.8 | 263.4 | 98 |

This table makes it possible to calculate the but-1-ene yield at the top of the column: 168.2% by mass, and the hydrogenation yield that is, the ratio of butanes in the effluents (top and bottom of the column)/butanes in the feed, which is 100.7% by mass.

It should also be noted that the amount of hydrogen in the effluents of the top and bottom of the column is nil.

These examples show that even when operations are carried out at a relatively low temperature, good but-1-ene yields are already obtained, with a low yield of hydrogenation products.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for obtaining but-1-ene from but-2-enes, comprising passing a feed containing at least one of the geometrical isomers of but-2-ene to a distillation zone linked with a hydro-isomerization zone located at least partly outside said distillation zone, the feed to the distillation zone being introduced to at least one level of the said distillation zone; passing a charge to the hydro-isomerization zone, said charge being withdrawn from at least one withdrawal level of the distillation zone; withdrawing an effluent from the hydro-isomerization zone and at least partly reintroducing said effluent into the distillation zone to at least one level of reintroduction; and withdrawing an overhead containing at least but-1-ene from the top of the distillation zone, and wherein a hydro-isomerization reaction is conducted at least partly in said hydro-isomerization zone located outside the distillation zone.

2. A process for obtaining but-1-ene from but-2-enes according to claim 1, wherein the hydro-isomerization reaction is carried out completely in a zone outside the distillation zone.

3. A process for obtaining but-1-ene from but-2-enes according to claim 2, wherein in that the hydro-isomerization carried out in a zone outside the distillation zone is carried out at an absolute pressure of about 1 to 70 bar at a temperature of about 0 to 250° C.

4. A process for obtaining but-1-ene from but-2-enes according to claim 1, wherein the hydro-isomerization reaction is carried out partly in at least one zone incorporated in the distillation zone and partly in at least one zone outside the distillation zone.

5. A process for obtaining but-1-ene from but-2-enes according to claim 4, wherein the hydro-isomerization carried out in a zone incorporated in the distillation zone is carried out at a temperature of about 0 to 250° C.

6. A process for obtaining but-1-ene from but-2-enes according to claim 4, wherein the hydro-isomerization carried out in a zone outside the distillation zone is carried out at an absolute pressure of about 1 to 70 bar and at a temperature of about 0 to 250° C.

7. A process for obtaining but-1-ene from but-2-enes according to claim 6, wherein the hydro-isomerization carried out in a zone incorporated in the distillation zone is carried out at a temperature of about 0 to 250° C.

8. A process for obtaining but-1-ene from but-2-enes according to claim 1, wherein distillation is carried out at an absolute pressure of about 1 to 50 bar, with a reflux ratio of about 1 to 70, with a temperature at the top of the distillation zone of about 0 to 200° C., and a temperature at the bottom of the distillation zone of about 5 to 250° C.

9. A process for obtaining but-1-ene from but-2-enes according to claim 1, wherein, in the hydro-isomerization zone, a supported catalyst is used containing at least one metal chosen from the group consisting of nickel and the noble metals of group VIII.

10. A process for obtaining but-1-ene from but-2-enes according to claim 1, further comprising a step for removing isobutene, said step being carried out before or after the linked step of distillation and hydro-isomerization.

11. A process for obtaining but-1-ene from but-2-enes according to claim 10, further comprising a step for removing isobutane, said step being carried out before or after the linked steps of distillation and hydro-isomerization.

12. A process for obtaining but-1-ene from but-2-enes according to claim 11, further comprising a step for removing butadiene, said step being carried out before or after the linked steps of distillation and hydro-isomerization.

13. A process for obtaining but-1-ene from but-2-enes according to claim 10, further comprising a step for removing butadiene, said step being carried out before or after the linked steps of distillation and hydro-isomerization.

14. A process for obtaining but-1-ene from but-2-enes according to claim 1, further comprising a step for removing isobutane, said step being carried out before or after the linked steps of distillation and hydro-isomerization.

15. A process for obtaining but-1-ene from but-2-enes according to claim 1, further comprising a step for removing butadiene, said step being carried out before or after the linked steps of distillation and hydro-isomerization.

16. A process according to claim 1, wherein the hydro-isomerization zone is operated at about 10° C. higher than the distillation zone.

17. A process according to claim 1, further comprising heating the charge withdrawn from the distillation zone before the charge is passed to hydro-isomerization zone.

18. A process according to claim 17, further comprising cooling the effluent from the hydro-isomerization zone before reintroducing said effluent to the distillation zone.

19. A process according to claim 1, further comprising cooling the effluent from the hydro-isomerization zone before reintroducing said effluent to the distillation zone.

20. A process for obtaining but-1-ene from but-2-enes according to claim 1, wherein said charge to said hydro-isomerization zone is withdrawn at an intermediate level of said distillation zone and said hydroisomerization zone being reintroduced at a level higher than said intemediate level of said distillation zone.

21. A process for obtaining but-1-ene from but-2-enes according to claim 20, wherein said hydro-isomerization zone is completely outside of said distillation zone.

22. A process for obtaining but-1-ene from but-2-enes according to claim 20, wherein said charge to said hydro-isomerization zone is withdrawn as a sidestream.

* * * * *